United States Patent [19]

Gorey et al.

[11] 4,004,449
[45] Jan. 25, 1977

[54] IMPACT SOUND STRESSING FOR SEMICONDUCTORS

[75] Inventors: Edward F. Gorey, Beacon; Guenter H. Schwuttke, Poughkeepsie, both of N.Y.

[73] Assignee: International Business Machines Corporation, Armonk, N.Y.

[22] Filed: June 30, 1975

[21] Appl. No.: 591,922

[52] U.S. Cl. .......................................... 73/12; 73/7
[51] Int. Cl.² ........................................ G01N 3/32
[58] Field of Search ............ 73/7, 12, 86, 69, 552, 73/104, 78

[56] References Cited
UNITED STATES PATENTS

| | | | |
|---|---|---|---|
| 1,961,333 | 6/1934 | Burns | 73/7 |
| 2,414,439 | 1/1947 | Brandon | 73/7 |
| 2,782,632 | 2/1957 | Klein et al. | 73/67.2 |
| 3,561,253 | 2/1971 | Dorman | 73/432 R X |
| 3,636,772 | 7/1973 | Bennett | 73/7 X |

*Primary Examiner*—Charles A. Ruehl
*Attorney, Agent, or Firm*—Sughrue, Rothwell, Mion, Zinn & Macpeak

[57] ABSTRACT

Apparatus for acoustical stressing of semiconductor wafers is disclosed, utilizing a number of small tungsten balls which are bounced on the surface of the wafer to be stressed. The movement of the tungsten balls is effectuated by clamping a wafer at one end of a conduit, the other end being attached to a high intensity loudspeaker. The loudspeaker is driven at resonant frequency of the clamped wafer and accordingly the tungsten balls bounce on the surface. This impact creates micro-cracks on the surface of the wafer and number and depth of these cracks can be controlled by power input and the number of tungsten balls utilized. Controlled stressing can thereby be accomplished both in terms of density of micro-cracks and location on the wafer.

Impact sound stressing finds utilization in the study of semi-conductor surfaces to determine effects of dislocations and micro-splits and in the evaluation of wafer polishing techniques. Structural changes in the original defect pattern due to oxidation can be studied and a cause and effect relationship between damage and oxidation established. The study of surface characteristics affecting many semi-conductor phenomena such as effective lifetime, noise, and contact potentials can be made in a controlled manner. Modern wafer polishing methods such as the cupric ion or silicon dioxide technique and others can be evaluated in terms of effectiveness of damage removal.

12 Claims, 6 Drawing Figures

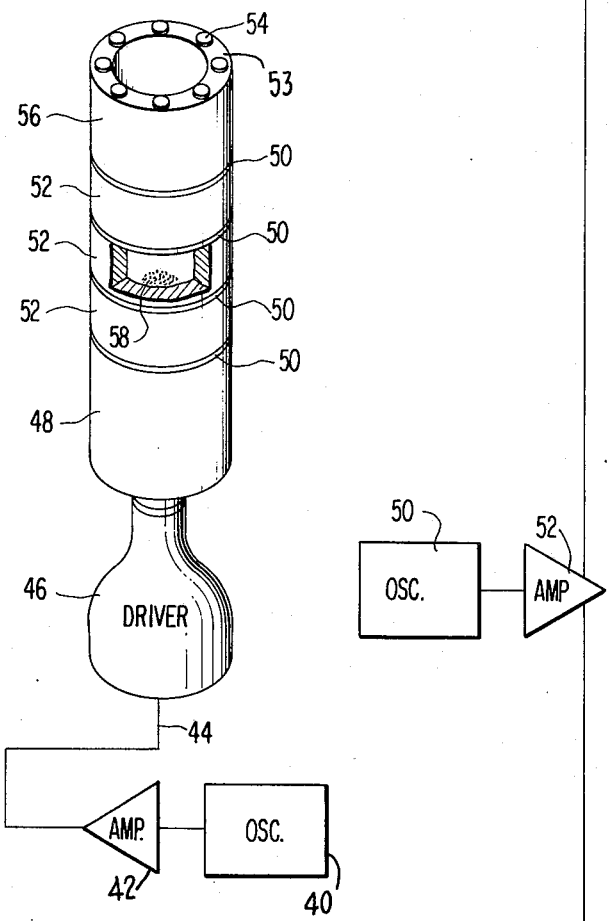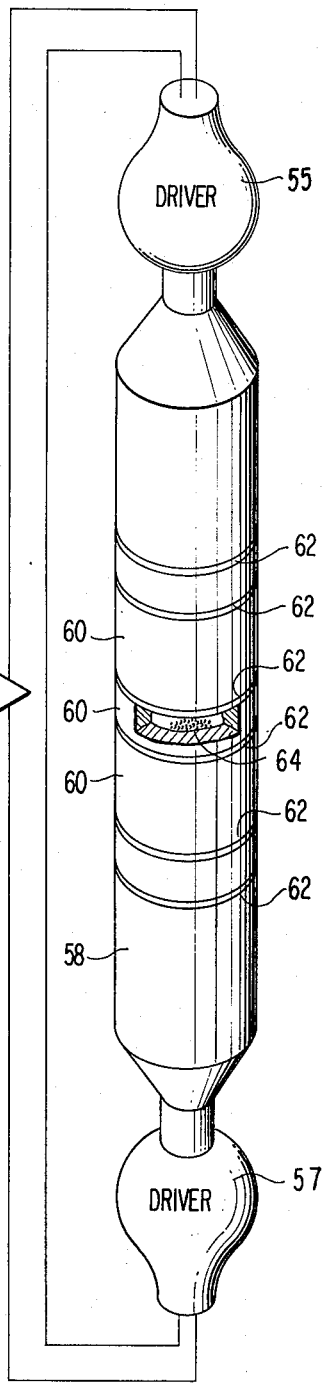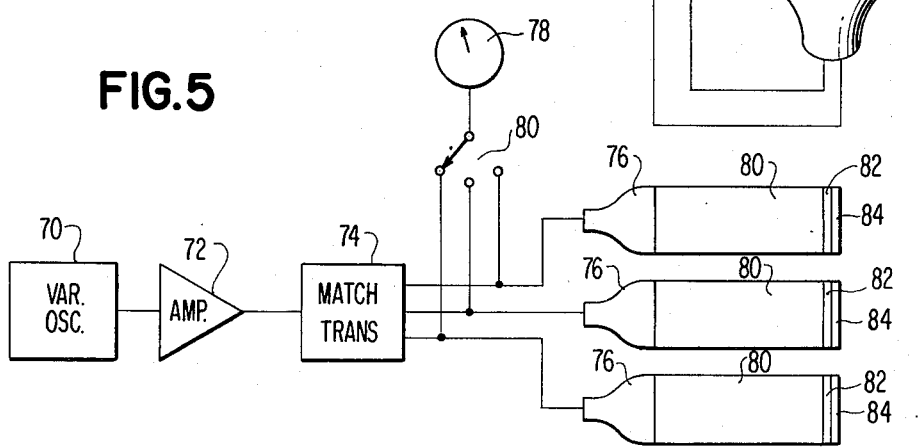

IMPACT SOUND STRESSING FOR SEMICONDUCTORS

This invention is related to an application entitled "Impact Sound Stressing for Semiconductor Devices" by G. H. Schwuttke and K. H. Yang, assigned to International Business Machines Corporation and filed on Sept. 10, 1975, Ser. No. 612,164.

BACKGROUND OF THE INVENTION

1. Field of the Invention

This invention relates to the treatment of semiconductor surfaces to induce micro-damage in a controlled manner.

2. Prior Art

Modern silicon technology has been able to provide the fabricator of semiconductor devices with nearly perfect silicon crystals that produce excellent $SiO_2$ interfaces as characterized through surface state density and minority carrier lifetime. The development of silicon technology has been accomplished mainly as a result of technological advances in manufacturing techniques as opposed to the utilization of well-established physical models of the nature of interface states and lifetime killing traps. As a result, this field is still one in which active interest occurs in terms of providing information on the insight into the generation of surface states and lifetime. Studies on the importance of residual mechanical damage on Si-$SiO_2$ interface quality have been recently reported in ARPA reports numbers 1–3 for contract No. DHC15-72-CO274. The need to impart mechanical damage to a controlled depth in the wafer and, alternatively, over controlled areas of the wafer becomes important in experiments on direct measurements of this mechanical damage and its influence on MOS capacitor properties.

Whenever semiconductor wafers are subjected to mechanical treatment, typically slicing, lapping, abrading, polishing, or sand-blasting, surface damage results. The nature of this damage has not always been understood and the correlation to semiconductor properties not fully developed. Some investigators have concluded that the damage consists entirely of cracks while others contend that dislocations are present. Surface damage of abraded silicon wafers is presented by Stickler and Booker, Phil. Mag. 8, 859 (1963), in which the authors examined single crystal silicon samples after the application of unidirectional abrasion. The abrasives used ranged from a 0.25 micron diamond to No. 240 SiC paper. By the use of transmission electron microscopy (TEM) this report demonstrated that damage varied in a progressive manner with the severity of the abrasive treatment, and ranged from rows of single dislocations to bands of dislocations and cracked material. The corresponding depth of damage ranged from 0.2 $\mu$m to 25 $\mu$m and for fine abrasion they observed anisotropy of damage. This feature, however, disappeared for coarse abrasive treatment. This report also noted that annealing changed the dislocation configurations as well as causing new dislocations to be propogated to relieve elastic strains.

Research such as the type above cited has led to general agreement that dislocations are formed whenever damaged semiconductor samples are annealed. The formation and propagation of dislocations materially alters yield rates of semiconductor devices and, accordingly, the importance of damage-free surfaces on high quality silicon is apparent. However, necessary mechanical operations such as polishing and cutting cannot be avoided and along with device processing makes the study of semiconductor surface properties important as a means of evaluating the performance of resulting devices. The prior art is completely devoid of any technique for inducing a known and controlled damage on wafer surfaces to enhance a study of damage characteristics both before and after device processing.

SUMMARY OF THE INVENTION

This invention produces damage in perfect silicon surfaces in a controlled manner to make it possible to study the influence of such damage on the Si-$SiO_2$ interface after device processing. The invention utilizes a new concept herein designated as Impact Sound Stressing (ISS). In its most basic form, a wafer is clamped on one end of a tube with the other end of the tube operably coupled to a source of acoustical power such as a loudspeaker. A number of hard, small balls are placed on the wafer, and the loudspeaker is driven at the resonant frequency of the wafer thereby causing the balls to bounce on the wafer surface. The bouncing can be controlled both in terms of location by masking, and time, to induce damage in a controlled manner. Impact sound stressing produces two damage features, a fine strongly directional abrasion leading to shallow grooves and the formation of Hertzian fracture cones. Subsequent device processing and testing assures that only the effect of impact sound stressing is measured and not any side effects that may arise as a result of wafer processing. Typical measurements include surface state density ($N_{ss}$), the energy distribution of surface state density $N_{ss}(\psi_{cB})$ and the generation lifetime ($\tau$). These measurements provide the researcher and quality control technician with valuable insight into undesirable processing effects, such as leaky oxides, impurity contamination and fixed charges accumulating in the oxide.

Accordingly, it is an object of this invention to provide a technique for damaging wafers in a known and controlled manner to determine interface properties.

It is a second object of this invention to provide an apparatus for the controlled damaging of silicon wafers.

It is another object of this invention to provide an apparatus for the degrading of the surface of silicon wafers to a controlled and uniform depth.

It is still a further object of this invention to provide an apparatus for the controlled degrading of a wafer surface at certain discrete locations of that surface.

Yet another object of this invention is to provide a unique method of introducing controlled damage into a silicon wafer for subsequent laboratory evaluation of the mechanical metallurgical properties therefrom.

Other objects and a full understanding of the present invention may be had by referring to the following description and claims taken in conjunction with the accompanying drawings.

BRIEF DESCRIPTION OF THE DRAWINGS

FIG. 3 shows a schematic diagram of a second preferred embodiment of this invention utilizing two separated speakers driven 180° out-of-phase.

FIG. 4 shows another preferred embodiment of this invention utilizing silicon wafers positioned in a back-to-back relationship utilizing a single speaker.

FIG. 5 shows still another preferred embodiment of this invention in which a multitude of speakers and amplifiers are utilized to effectuate impact sound stressing on a number of samples.

DETAILED DESCRIPTION OF THE PREFERRED EMBODIMENTS

Figure 1:
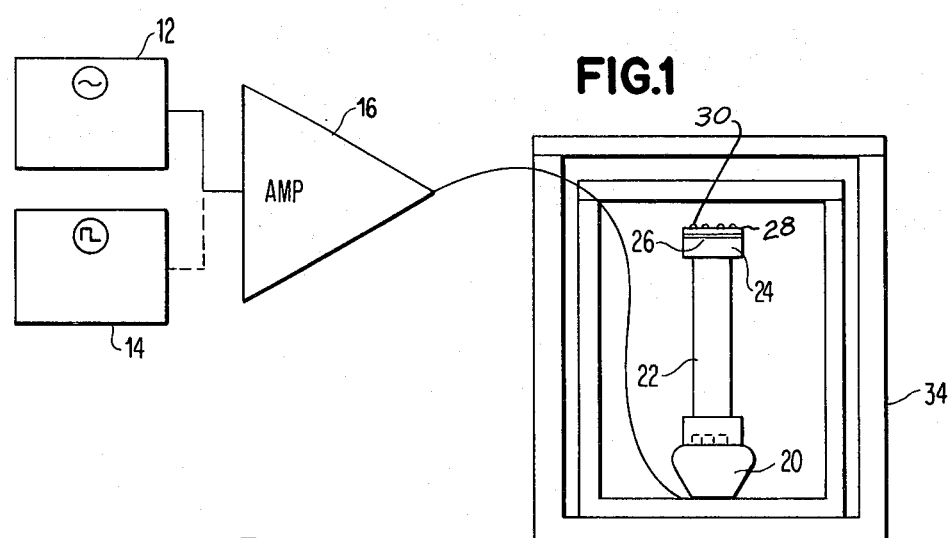
FIG. 1 is a schematic drawing of the impact-sound stressing apparatus according to this invention.

Referring now to FIG. 1 a schematic showing the basic structure of the impact-sound stressing apparatus is depicted. As shown in FIG. 1, the basic electrical input into this system is by means of either a HP 651 B oscillator 12 or a Wavetek Model 142 Square Wave Generator 14, either one of these oscillators selectively coupled to an amplifier 16, typically a McIntosh Model M 1-300 Power Amplifier, by means of suitable electrical connections 18. The amplifier output is carried to an acoustic driver 20, typically an Atlas PD-60T 60 watt loudspeaker which is commonly utilized in public address systems. Mounted on the speaker, using threads typically utilized for holding the loudspeaker trumpet which is disconnected for this purpose, is a tube of PVC pipe approximately 30 centimeters in length. The tube 22 has a fitting 24 on top of which a silicon wafer 26 is placed.

Figure 2:
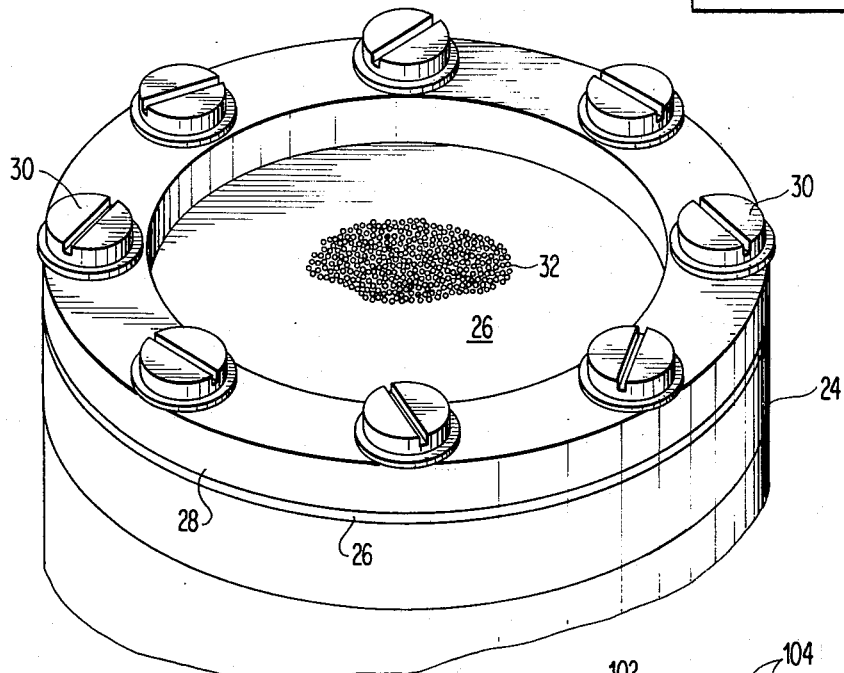
FIG. 2 is a perspective drawing showing a close-up of a silicon wafer loaded with a number of balls at the top section of the impact-sound stressing structure.

Referring to FIG. 2, the details of the top construction of the tube 22 with top fitting 24 and silicon wafer 26 are shown in greater detail. In particular, the wafer 26 is placed on a recess of the tube 24 and held in place by means of a Teflon ring 28. The Teflon ring may be bolted into position on fitting 24 by means of suitable bolts 30 or any other convenient hold-down technique. Disposed on the surface of the silicon wafer 26 are a number of balls 32, typically tungsten, each having a diameter in the order of 300 $\mu$m. To prevent the loss of the balls 32 during the vibration of the silicon wafer, a piece of filter paper or another wafer, not shown, may be placed over the top of the ring 28. The completed speaker assembly is placed in a sound-proof box 34, as shown in FIG. 1. Utilizing the structure shown in FIGS. 1 and 2, generation of high or low densities or micro-splits in the surface of the silicon wafer 26 can be generated in the form of fracture cones. These Hertzian fracture cones are produced in a range of approximately 50 $\mu$m in diameter and may penetrate a few microns into the bulk of the silicon or as deep as 15–20 $\mu$m. The fracture cones are induced in the silicon surface by impacting the wafer surface 26 with the balls 32 under acoustic stressing. The acoustic stressing is accomplished by means of the high intensity driver 20 driven at the resonant frequency typically 1.38 kHz, of the clamped wafer. Typical operative conditions call for the generation of this frequency at 40 watts for approximately 5 minutes. Consequently, the tungsten balls impacting the wafer surface replicate an acoustic mode pattern of the clamped vibrating wafer to a Hertzian fracture cone pattern.

It will be appreciated that the density of the microcracks thereby achieved is a function of the vibration time, the number of tungsten balls on the wafer and the power input to the speaker. Densities of $10^6$ splits per $cm^2$ are easily achieved without breaking the wafer. Also, approximately 800 balls are utilized in a typical operation. These balls may be made of tungsten or other suitable material.

Referring now to FIG. 3, a second preferred embodiment utilizing a back-to-back configuration of silicon wafers is disclosed. In this embodiment, the oscillator 40, typically an HP 651B or Wavetek Model 142, is used to provide an input to a power amplifier 42. The amplifier output on line 44 is fed to a loudspeaker 46, typically an Atlas PD 60T driver. As in the prior example, a hollow pipe of PVC tubing 48 is affixed to the threads holding the loudspeaker trumpet which is disconnected for this purpose. A series of silicon wafers 50 are stacked on the tube 48 by means of spacers 52 held in place by a ring 56 and a series of long bolts 54 which couple the end plate 53 and spacers 52 to the tube assembly 48. Disposed at appropriate locations between the wafers 50, a number of balls 58 are located such that when the driver 46 is powered, the balls 58 are caused to vibrate between the adjacent sides of wafers 50. Operating frequency of the oscillator 40 and power of the amplifier 42 then becomes a function of the degree of stressing required in the wafers. Also, the number of wafers to be worked, at any one time is materially enhanced over the embodiment as set forth in FIGS. 1 and 2.

Referring now to FIG. 4, still another preferred embodiment of the invention is shown. In FIG. 4, two speakers are driven 180° out-of-phase to provide increased power and efficiency for sound stressing as a result of vibration by balls placed between the adjacent sides of silicon wafers. As in the prior embodiments, an oscillator 50 is used to provide a suitable waveform to power amplifier 52. In this embodiment, two loudspeaker drivers, again typically Atlas PD 60T drivers 55 and 57, are disposed at ends of a PVC tube 58 which is threaded to the threads normally holding the loudspeaker trumpet for each driver. A series of spacers 60 are used to separate silicon wafers 62 which have a number of balls 64, typically 300 $\mu$m diameter tungsten located to vibrate between adjacent sides of the wafers. Although, not shown, conventional clamp down or holding devices may be utilized to effectuate a locking relationship between the spacers 60 and the tubing 58. The speakers 55 and 57, are driven in a push-pull arrangement, that is, 180° out-of-phase and utilizing this technique, the number of silicon wafers which may be sound stressed is again materially increased over the other two previously described embodiments.

Turning now to FIG. 5, a multiple sound stressing system is shown. In this embodiment, a variable frequency oscillator 70, typically an HP 651B test oscillator or simulator is used as a power input to amplifier 72. In place of the variable oscillator, a wobbler or noise generator may be substituted. The power amplifier 72 is typically a 350 watt power amplifier such as a Bogen NT B250. While one such amplifier is shown in FIG. 5, any number of amplifiers may be used in a parallel arrangement. Also, it is important to note that in this configuration automatic gain control on the amplifier should be used to keep the power constant to each speaker. Coupling the amplifier 72 to the speakers is an optional matching transformer 74. The function of the matching transformer 74 is to match any number of speakers with any number of power amplifiers in a manner conventionally known and well understood in the art. As in the prior examples, the speakers 76 are Atlas PD 60T drivers. A watt meter 78 may be selectively coupled to each speaker at location 80 by means of conventional switching and coupling techniques.

The loudspeaker trumpet of each speaker 76 is disconnected and the threads normally holding that trumpet are used to mount a length of PVC pipe 80 to each speaker. In a manner similar to the embodiment shown in FIG. 1, a wafer of silicon 82 is affixed in the recess of the PVC tubing at the opposite end from the speaker and a ring 84 is used to hold the wafer in place. Not shown in FIG. 5 are the balls, typically numbering approximately 800 in each recess to vibrate upon the application of power. Using this configuration, as shown in FIG. 5, up to 10 speakers may be used at 25 watts of power for each speaker.

Using the concept of impact sound stressing, damage to silicon wafers can be controlled in a uniform manner. The amount of damage produced is a function of a number of balls vibrating on the wafer surface and is also dependent on the power input to the loudspeaker. Also, using conventional masking techniques on the silicon wafer, localized areas can be exposed for damage while the remainder of the wafer is insulated from vibration of the balls. With the damage produced before processing in such a controlled manner, it is possible to study the influence of micro-damage on the Si-SiO$_2$ interface after device processing. Utilizing impact sound stressing, the physical crystallography of dislocations and micro-splits can be examined in greater detail.

Figure 6:
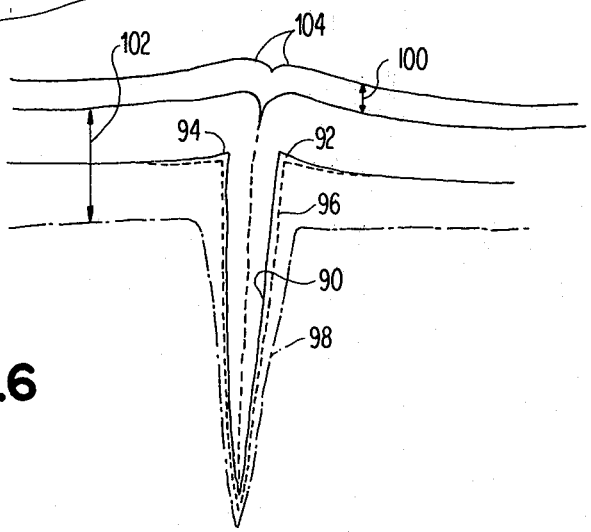
FIG. 6 is a schematic diagram showing a model of the oxide and aluminum layers at a mirco-crack in a silicon wafer which has been damaged utilizing the technique of impact-sound stressing.

One characteristic example is the modeling of oxide and aluminum layers at the micro-crack in a silico wafer. As shown in FIG. 6, the original fracture is shown along line 90 as the result of the impact of a ball on the bare silicon surface. This fracture is generally in the order of approximately 6 microns in depth. The Hertzian fracture cone is clearly shown in FIG. 6 characterized by raised corners 92 at the situs of the fracture following annealing, the fracture assumes a path as shown along the line 96 and the oxide silicon boundary shown as line 98. It is noted that the silicon oxide boundary would appear to have a wider fracture with decreasing depth. The model shown in FIG. 6 assumes that the outside growth rate into the material from the surface is greater than that from the bottom of the crack. Hence, the reduced growth rate downward for the fracture bottom would be due to the increasing oxide thickness and the fracture as it is filled in. The resulting aluminum layer is shown as extending to a depth indicated at 100 over the previously resulting oxide layer shown at a depth indicated by 102. A pillowing effect shown by protrusions 104 in the aluminum layer is due to the unequal oxidation rates at the crack and silicon surface. This pillowing effect occurs at the edges of the fracture, which are in fact, the junctions of two surfaces of different crystallographic orientation, namely, the sample surface and the fracture walls. Also, the apparent width and depth of fracture outlines after oxidation including their possible complete disappearance is also dependent on the total oxide thickness 102 above the original surface. It is recognized that a fracture filling up with oxide as oxidation proceeds, disappears when a certain oxide thickness is reached. The model shown in FIG. 6 illustrates how a disturbance at the junction can be propagated and enhanced.

Also, it is possible to evaluate the interface properties of impactsound stressed silicon wafers not only for data relevant to determinations of surface characterization, as shown in FIG. 6, but also to provide insight to undesirable processing effects as a result of device formation.

A typical experiment utilizes ten wafers, sound stressed with 800 standard 0.3 mm tungsten balls on the wafer frontside. The sound stressing lasts more than 5 minutes at a power level of 40 watts. The wafers were subsequently X-ray topographed to ascertain the defect level and defect distribution and then were divided into five groups for repolishing. Different controlled amounts of material were removed in each group through repolishing. The wafers are then processed to contain 36 circular MOS capacitors each 1.5 mm in diameter. Prior to oxidation, the wafers are cleaned using $NH_4$-$H_2O_2$, $HCl$-$H_2O_2$ and HF solutions. A 5,000 angstrom thick oxide is grown at 1000° C using a dry-wet-dry oxidation cycle and aluminum metallurgy is used to form the capacitors. Following metallization, the wafers are annealed for 15 minutes at 400° C.

The generation lifetime of six different capacitors per wafer are typically measured. These MOS capacitors are changed by pulsing the structure from accumulation into deep depletion and then measuring the capacitance (at 1 MHz) as a function of time. It has been shown that the time constant T for the capacitance relaxation from the deep depletion value $C_D$ to the equilibrium value $C_E$ is related to lifetime of minority carriers in the depletion region [see Heimann, IEEE Trans. ED-14, p. 781 (1967)]. The following table summarizes the results and it is interesting to note that complete lifetime recovery is achieved in the group V wafers.

| Group No. | Repolish ($\mu$m) | Ave. | ($\mu$ Sec.) High | Low |
|---|---|---|---|---|
| I | 2 | 0.224 | 0.6 | 0.028 |
| II | 4 | 0.96 | 2.42 | 0.18 |
| III | 8 | 42.5 | 137 | 6.6 |
| IV | 24 | 432 | 1160 | 6.9 |
| V | 30 | 1366 | 1916 | 80.0 |

Control wafers processed undamaged by impact sound stressing also yielded a lifetime better than 1000$\mu$ sec. The calculation of the generation lifetimes provides an indication of the characteristics of the bulk silicon wafer.

Additional electrical measurements include the measurement of surface state density ($N_{ss}$) and the energy distribution of surface state density $N_{ss}(\psi_{cB})$. Surface state density can be extracted from plots of the high and low frequency C-V curves using a quasi-static (sweep rate between 50 and 100 mV/Sec.) low frequency curve and a 1 MHz high frequency curve on the same MOS capacitor. These values are evaluated in a manner suggested by Castagner, C. R. Acad. Sc. Paris, t. 267, Series B. 866, (1968) to obtain surface state density $N_{ss}$ and its distribution as a function of the surface potential $\psi_{cB}$ with respect to the conduction band. The data can be computerized and compared to control wafer data.

Impact sound stressing introduces micro-damage on wafer surfaces in a controlled and reproducible manner. The influence of such microdamage can be studied in an orderly manner to ascertain influence on the Si-SiO$_2$ interface after device processing and also the effectiveness of damage removal of modern polishing techniques. The need for reproducible results in the evaluation of surface characteristics of semiconductor devices and wafer polishing techniques is thereby achieved by the use of impact sound stressing.

While the foregoing preferred embodiments of the invention have been discussed, it is to be understood that other changes and improvements would be readily apparent without departing from the scope and nature of the invention.

What is claimed is:

1. A method for micro-damaging a surface of a semiconductor wafer in a controlled manner comprising the steps of, placing a plurality of loose spherical shaped objects on one surface of said wafer and acoustically vibrating said wafer to micro-damage said surface by the bouncing of said objects on the surface.

2. The method of claim 1 wherein the wafer is acoustically vibrated at the resonant frequency of the wafer.

3. The method of claim 1 wherein the power of said acoustical vibrations may be varied.

4. The method of claim 1 wherein said wafer is clamped onto a conduit coupled to a source of acoustic vibration and a second wafer is clamped in said conduit in a back-to-back relationship with said wafer such that the acoustical vibrations cause the spherical objects to bounce against both of said wafers.

5. The method of claim 1 wherein said wafer is masked prior to placing said spherical objects such that selected areas of the surface of said wafer are exposed for controlled damage.

6. The method of claim 1 wherein two sources of acoustic vibration are placed on opposite ends of a conduit, clamping said wafer at a location within the conduit and driving said sources in a push-pull arrangement to vibrate said wafer.

7. Apparatus for micro-damaging a surface of a semiconductor wafer in a controlled manner comprising; a source of acoustical energy, means coupling said source to said wafer for transmission of acoustic energy from said source to said wafer, and a plurality of loose spherical shaped objects on one surface of said wafer, whereby, the application of acoustical energy to said wafer causes said wafer to vibrate thereby bouncing said spherical objects on the surface of said wafer.

8. The apparatus of claim 7 wherein said vibration is at the resonant frequency of said wafer.

9. The apparatus of claim 8 wherein said loose spherical objects are balls of tungsten in the order of 300$\mu$m in diameter.

10. The apparatus of claim 7 wherein said wafer is clamped to said coupling means by means of a cover plate secured to said coupling means.

11. The apparatus of claim 7 wherein said source of acoustical energy comprises: an oscillator, an amplifier coupled to said oscillator and a loudspeaker coupled to the amplifier.

12. Apparatus for creating micro-damage in the surface of a semiconductor wafer in a controlled amount comprising, a plurality of spherical shaped objects disposed on said surface for movement relative to said wafer and, means for vibrating said wafer such that said vibrations cause said objects to bounce on said surface inducing micro-damage in the surface.

* * * * *